(12) United States Patent
Feldman et al.

(10) Patent No.: US 10,085,646 B2
(45) Date of Patent: Oct. 2, 2018

(54) CONTACT-TYPE ENDOSCOPE SERS PROBE, AND RELATED METHODS

(71) Applicants: Martin Feldman, Baton Rouge, LA (US); Dooyoung Hah, Baton Rouge, LA (US)

(72) Inventors: Martin Feldman, Baton Rouge, LA (US); Dooyoung Hah, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 350 days.

(21) Appl. No.: 14/721,953

(22) Filed: May 26, 2015

(65) Prior Publication Data

US 2015/0335249 A1   Nov. 26, 2015

Related U.S. Application Data

(60) Provisional application No. 62/002,977, filed on May 26, 2014.

(51) Int. Cl.
| | |
|---|---|
| *A61B 1/06* | (2006.01) |
| *A61B 5/00* | (2006.01) |
| *G01N 21/65* | (2006.01) |
| *A61B 1/00* | (2006.01) |
| *G01J 3/44* | (2006.01) |

(Continued)

(52) U.S. Cl.
CPC ........... *A61B 5/0075* (2013.01); *A61B 1/0011* (2013.01); *A61B 1/06* (2013.01); *A61B 1/0661* (2013.01); *A61B 5/0084* (2013.01); *G01J 3/0205* (2013.01); *G01J 3/44* (2013.01); *G01N 21/658* (2013.01); *A61B 1/002* (2013.01)

(58) Field of Classification Search
CPC ....... A61B 5/0075; A61B 1/06; A61B 5/0084; A61B 1/0011; A61B 1/0661; A61B 1/002; G01J 3/0205; G01J 3/44; G01N 21/658

See application file for complete search history.

(56) References Cited

U.S. PATENT DOCUMENTS

| | | |
|---|---|---|
| 5,255,067 A | 10/1993 | Carrabba et al. |
| 6,406,777 B1 | 6/2002 | Boss et al. |

(Continued)

OTHER PUBLICATIONS

Liu et al., "Nanowell surface enhanced Raman scattering arrays fabricated by soft lithography for label free biomolecular detections in integrated microfluidics," Appl. Phys. Lett. 87, 074101 (2005).*

(Continued)

*Primary Examiner* — Rex R Holmes
(74) *Attorney, Agent, or Firm* — Venable LLP; Steven J. Schwarz; Laura G. Remus

(57) ABSTRACT

A contact-type endoscope surface enhanced Raman scattering (SERS) probe includes a gradient-index (GRIN) lens, a transparent substrate adhered to the GRIN lens, and a rough metallic layer adhered to an opposite side of the transparent substrate from the GRIN lens. The GRIN lens focuses light from a Raman spectrometer onto the rough metallic layer, and the rough metallic layer is positioned at the distal end of the contact-type endoscope SERS probe.

5 Claims, 16 Drawing Sheets

(51) Int. Cl.
  *G01J 3/02* (2006.01)
  *A61B 1/002* (2006.01)

(56) References Cited

U.S. PATENT DOCUMENTS

| | | | |
|---|---|---|---|
| 7,453,565 | B2 | 11/2008 | Wang et al. |
| 7,898,658 | B2 | 3/2011 | Moskovits et al. |
| 8,547,549 | B2 | 10/2013 | Kuo et al. |
| 8,576,394 | B2 | 11/2013 | Biris et al. |
| 8,767,202 | B2 | 7/2014 | Schmidt et al. |
| 2006/0017918 | A1* | 1/2006 | Cullum ............... G01N 21/658 356/301 |
| 2010/0149529 | A1 | 6/2010 | Biris et al. |
| 2010/0256469 | A1* | 10/2010 | Cook ................. A61B 5/14542 600/323 |
| 2014/0081150 | A1 | 3/2014 | Chu et al. |
| 2017/0112380 | A1* | 4/2017 | Jeong ................. A61B 5/0071 |

OTHER PUBLICATIONS

Choi et al., "Surface-enhanced Raman nanodomes," 2010 Nanotechnology 21 415301.
Das et al., "Nano-Patterned SERS substrate: application for protein analysis vs. temperature," Biosensors and Bioelectronics, vol. 24, Iss. 6, 2009, pp. 1693-1699.
Jeon et al., "Shape control of Ag nanostructures for practical SERS substrates," ACS Appl. Mater. Interfaces, 2013, 5 (2), pp. 243-248.
Kiraly et al., "Multifunctional porous silicon nanopillar arrays: antireflection, superhydrophobicity, photoluminescence, and surface-enhanced Raman scattering," 2013 Nanotechnology 24 245704.
Liu et al., "Nanowell surface enhanced Raman scattering arrays fabricated by soft lithography for label free biomolecular detections in inte rated microfluidics," Appl. Phys. Lett. 87, 074101 (2005).
Miyagawa et al., "Surface-enhanced Raman scattering from gold deposited mesoporous silicon," physica status solidi (a), vol. 208, Iss. 6, pp. 1471-1474, Jun. 2011.
Oh et al., "Glass nanopillar arrays with nanogap-rich silver nanoislands for highly intense surface enhanced Raman scattering," Adv Mater. May 2, 2012; 24(17): 2234-7.
Qian et al., "Large surface enhanced Raman scattering enhancements from fracture surfaces of nanoporous gold," Appl. Phys. Lett. 92, 093113 (2008).
Shevchenko et al., "Large-area nanostructured substrates for surface enhanced Raman spectroscopy," Appl. Phys. Lett. 100, 171913 (2012).
Wang et al., "High directivity optical antenna substrates for surface enhanced Raman scattering," Advanced Materials 2012; 24(32):4376-80.
Fleischmann M., Hendra P. J., and McQuillan A., Chem. Phys. Lett. 26, 163 (1974).
Gersten J. I., J. Chem. Phys. 72, 5779 (1980).10.1063/1.439002.
Hildebrandt P. and Stockburger M., J. Phys. Chem. 88, 5935 (1984).
J. Kim et. al./ Vac. Sci. Technol., vol. B-31, No. 6, Nov./Dec. 2013.
Kudelski A. and Pettinger B., Chem. Phys. Lett. 383, 76 (2004).
Kudelski A., Chem. Phys. Lett. 414, 271 (2005).
Liu G. L. and Lee L. P., Appl. Phys. Lett. 87, 074101 (2005).
Malempati P. R., Master's thesis, Louisiana State University (2011).
Nie S. M. and Emory S. R., Science 275, 1102 (1997).
Norland Optical Adhesive 68, Edmund Optics America, Barrington, NJ.
Van Duyne R. P., J. Phys. (Paris) 38, C5-239 (1977).
Wang Z. and Rothberg L. J., J. Phys. Chem. B 109, 3387 (2005).
Weiss A. and Haran G., J. Phys. Chem. B 105, 12348 (2001).
LabRAM Raman spectrometer, HORIBA Scientific, Edison, NJ, accessed from the Internet on May 26, 2015.
Olympus ultra-long working distance MS plan 50X objective, Olympus Corporation, Center Valley, PA, accessed from the Internet on May 26, 2015.

* cited by examiner

|  | NOT ETCHED | | ETCHED | | STIR ETCHED | |
|---|---|---|---|---|---|---|
|  | FRONT | BACK | FRONT | BACK | FRONT | BACK |
| ALUMINUM FOIL | 210 | 290 | 220 | 290 | 220 | 220 |
| PELLET | 210 |  | 450 |  | 440 |  |
| STOCK | 260 |  | 330 |  | 310 |  |
| FOIL PLUS GOLD | 520 | 540 | 1360 | 1550 | 4700 | 12700 |
| PELLET PLUS GOLD |  |  | 5200 |  |  |  |
| EPOXY PLUS GOLD |  |  | 1150 |  | 1700 | 1250 |

CONCENTRATION (μM)

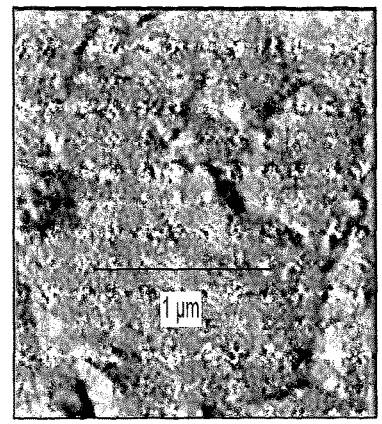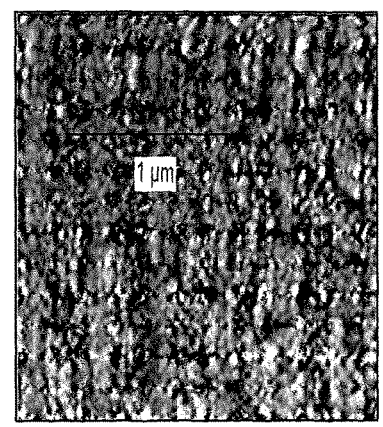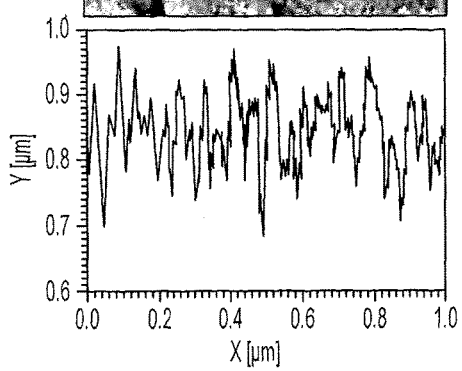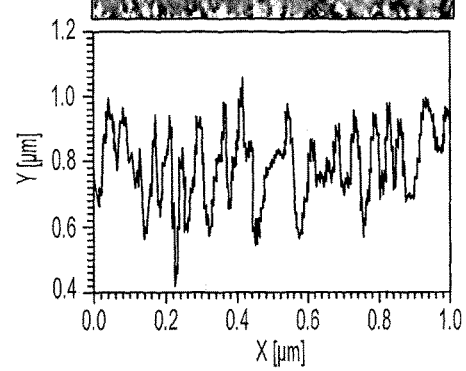
FIG. 16A    FIG. 16B
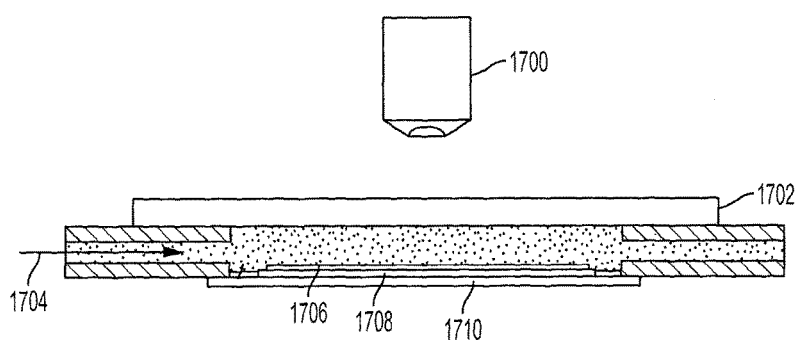
FIG. 17

CONTACT-TYPE ENDOSCOPE SERS PROBE, AND RELATED METHODS

This application claims priority to U.S. Provisional Application No. 62/002,977 filed May 26, 2014, the entire content of which is hereby incorporated by reference.

This invention was made with government support under Grant No. 1R03EB012519-01A1 awarded by the National Institutes of Health. The government has certain rights in this invention.

BACKGROUND

1. Technical Field

Embodiments of the claimed invention relate generally to surface enhanced Raman scattering (SERS), and more particularly, to a contact-type endoscope SERS probe and related methods.

2. Discussion of Related Art

Molecular imaging is an emerging branch of advanced biomedical imaging techniques. It plays a particularly significant role when it is difficult to discern the stage of disease by conventional optical or ultrasonic imaging. It provides crucial information for the biochemical study of the target tissues by reading molecular signatures without necessarily requiring a physical biopsy.

Among various modalities in molecular imaging, Raman spectroscopy (RS) is particularly interesting because it does not require flourophores, and therefore induces minimal alteration to the targeted tissue. Conventional Raman scattering is therefore a common technique for detecting and identifying complex molecular samples. However, regular RS tends to have very poor sensitivity. One remedy for this problem is surface enhanced Raman scattering (SERS). In SERS, the analytes are placed in close proximity to either nanometallic particles or a metallic surface with nanometer-scale roughness. Placing the nanorough metallic surface close to the sample can greatly enhance the Raman signal.[1-5] However, existing procedures for SERS imaging of a sample typically require the sample to be situated between the Raman spectrometer and the nanorough metallic surface. In most cases the sample must be biopsied in order to meet this requirement.

SUMMARY

According to some embodiments of the present invention, a contact-type endoscope surface enhanced Raman scattering (SERS) probe includes a gradient-index (GRIN) lens, a transparent substrate adhered to the GRIN lens, and a rough metallic layer adhered to an opposite side of the transparent substrate from the GRIN lens. The GRIN lens focuses light from a Raman spectrometer onto the rough metallic layer, and the rough metallic layer is positioned at the distal end of the contact-type endoscope SERS probe.

According to some embodiments of the present invention, a system for contact-type endoscope SERS includes a Raman spectrometer, and a probe having a proximal end and a distal end. The probe includes a GRIN lens, a transparent substrate adhered to the GRIN lens, and a rough metallic layer adhered to an opposite side of the transparent substrate from the GRIN lens. The system for contact-type endoscope SERS further includes an articulated arm comprising a plurality of mirrors for reflecting illumination light from the Raman spectrometer to the probe, and for reflecting scattered light from the probe to the Raman spectrometer. The GRIN lens focuses the illumination light from the Raman spectrometer onto the rough metallic layer.

According to some embodiments of the present invention, a method for producing a contact-type endoscope SERS probe includes depositing a layer of gold on aluminum foil, bonding the layer of gold on aluminum foil to a GRIN lens using a transparent epoxy, and etching the GRIN lens with the transparent epoxy and the layer of gold on aluminum foil to remove the aluminum foil.

BRIEF DESCRIPTION OF THE DRAWINGS

Further objectives and advantages will become apparent from a consideration of the description, drawings, and examples.

FIG. 16A shows an AFM image of 40 nm of gold on an epoxy substrate cast on a dry etched wafer, and the height distributions across the marked 1 micron line are shown below;

FIG. 16B shows an AFM image of 40 nm of gold on an epoxy substrate cast on a both wet and dry etched wafer, and the height distributions across the marked 1 micron line are shown below;

FIG. 17 illustrates a test cell with a clear epoxy substrate sandwiched between a microscope slide and a cover slip;

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Raman spectra have been used to identify substances for many years. The generally weak Raman signal levels can be significantly enhanced when the specimen is in contact with a rough metallic surface. Embodiments of the invention extend this surface enhanced Raman (SER) capability to an endoscopic probe, so that samples may be studied in vivo, rather than removed and placed on a microscope stage.

Figure 1:
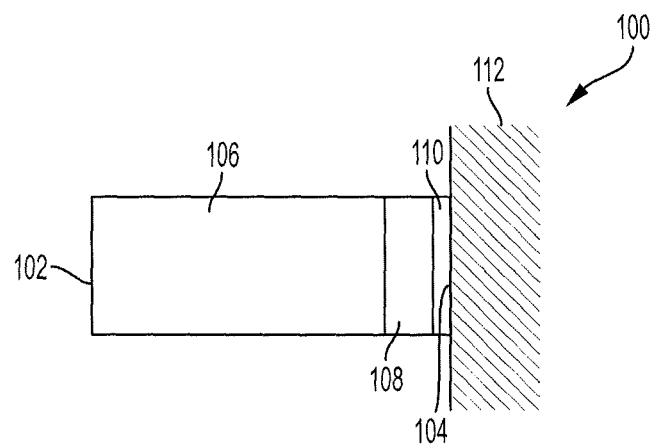
FIG. 1 is a schematic illustration of a contact-type endoscope surface enhanced Raman scattering (SERS) probe according to some embodiments of the current invention.

FIG. 1 is a schematic illustration of a contact-type endoscope surface enhanced Raman scattering (SERS) probe 100 according to some embodiments of the current invention. The probe 100 has a proximal end 102 and a distal end 104, and includes a gradient-index (GRIN) lens 106, a transparent substrate 108 adhered to the GRIN lens 106, and a rough metallic layer 110 adhered to an opposite side of the transparent substrate 108 from the GRIN lens 106. The GRIN lens 106 focuses light from a Raman spectrometer onto the rough metallic layer 110. The rough metallic layer 110 is positioned at the distal end 104 of the contact-type endoscope SERS probe 100. The rough metallic layer 110 at the distal end 104 of the contact-type endoscope SERS probe 100 can be placed into contact with a region of interest 112.

According to some embodiments of the invention, the GRIN lens is a π/2 GRIN lens. The GRIN lens can have a diameter that is between about 0.5 mm and about 5 mm according to some embodiments, and between about 0.5 mm and about 2 mm according to some additional embodiments. The GRIN lens can have a numerical aperture between about 0.1 and about 0.5 according to some embodiments.

Further concepts of the invention are described below with reference to particular examples. The general concepts of the current invention are not limited to the particular examples.

EXAMPLES

Figure 2:
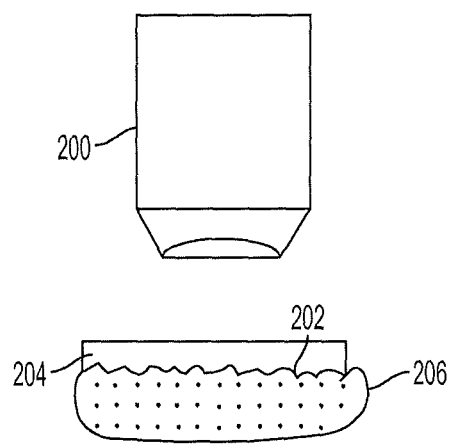
FIG. 2 illustrates how surface enhanced Raman (SER) spectra can be obtained through a rough gold film on a transparent substrate.

SER spectra have been obtained through a rough gold film on a transparent substrate, so that access was needed to only one side of the sample.[6] This concept is illustrated in FIG. 2, and is described in more detail below. FIG. 2 shows a microscope objective 200 that is part of a Raman spectrometer. The microscope objective 200 focuses light from the spectrometer onto a rough gold surface 202 adhered to a transparent substrate 204. The rough gold surface 202 is in contact with a region of interest 206.

Figure 3:
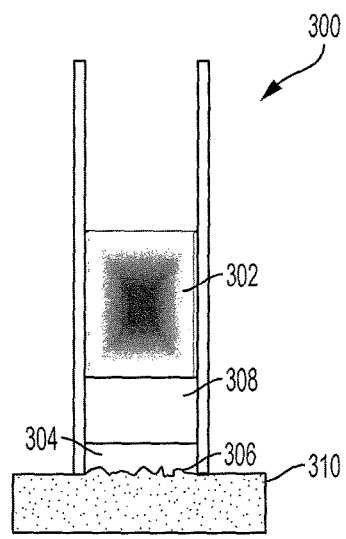
FIG. 3 shows a SERS probe with a graded index (GRIN) lens replacing the microscope objective in a Raman spectrometer.

According to some embodiments of the invention, a graded index (GRIN) lens replaces a microscope objective in a Raman spectrometer, as shown in FIG. 3. In the example of FIG. 3, a SERS probe 300 includes a GRIN lens 302 with a transparent substrate 304 adhered to the distal end of the GRIN lens 302. A rough metallic layer 306 is permanently adhered to the end of the transparent substrate 304 opposite the GRIN lens 302. A glue 308, for example, a transparent UV curing epoxy or other transparent adhesive, may be used to fix the substrate to the GRIN lens. Alternatively, the transparent substrate 304 may have adhesive properties that allow it to be directly adhered to the GRIN lens 302, without the need to for an additional glue 308.

During use, the rough metallic layer 306 is placed into contact with the region of interest 310. In the example of FIG. 3, the GRIN lens can have a diameter of about 1-2 mm that lends itself to incorporation into a needle-like endoscopic probe. The GRIN lens can also have a numerical aperture (NA) that is comparable to that of a 10× microscope objective, for example, the NA can be between about 0.1 and about 0.5. According to some embodiments, the NA can be between about 0.25 and about 0.35. FIG. 3 illustrates a fixed focus probe, since once the GRIN lens is focused on the rough metallic film 306, no further adjustment is needed. However, focusing capability can also be included in the SERS probe 300.

Figure 4:
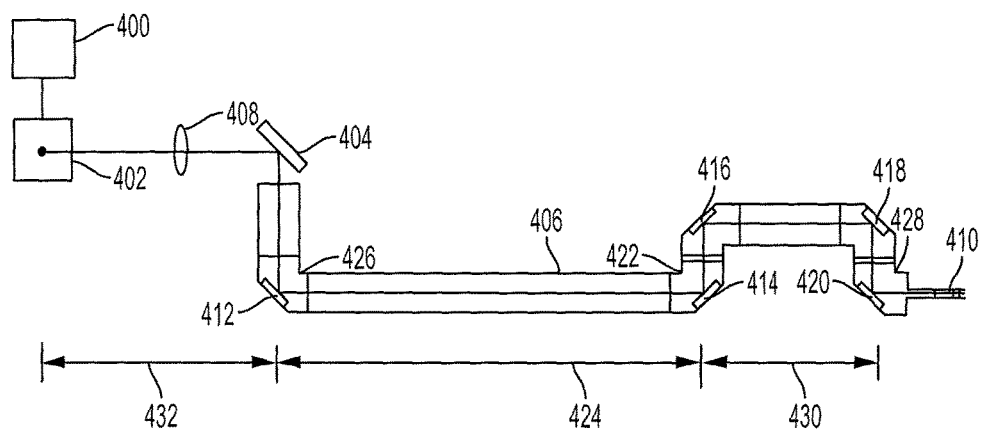
FIG. 4 shows a contact-type endoscope SERS probe with an articulated arm according to some embodiments of the invention.

It may be useful in clinical applications for the probe to be capable of pointing in any direction at any point within a sizable working volume. According to some embodiments, this may be accomplished by coupling the GRIN lens to the spectrometer with a single mode optical fiber. However, the background signal from the fiber masks the Raman signal from the probe. While hollow core optical fibers minimize the background signal, single mode fibers are generally limited in numerical aperture, which minimizes the Raman signal. Therefore, an articulated arm can be constructed as shown in FIG. 4. In the example of FIG. 4, the microscope objective of a Raman spectrometer 400 is removed and a mirror 402 is placed on the spectrometer stage. The spectrometer can be, for example, a Horiba LabRAM spectrometer, and the light exiting the spectrometer can be a slightly diverging 633 nm HeNe laser beam. The invention is not limited to this laser beam. Other lasers having other wavelengths can be used, for example, a neodymium-doped yttrium aluminum garnet (YAG) laser with a 1064 nm wavelength.

The mirror 402 placed on the spectrometer stage directs light to a second mirror 404 that directs the beam down the axis of the arm 406. The second mirror 404 may be fixed to a support base of the arm 406. A lens 408 can compensate for the slight divergence of the beam exiting the spectrometer when the microscope objective in the beam line is removed. The lens 408 can ensure that the beam matches the diameter of the downstream optics so that the GRIN lens 410 is filled. The beam can be brought to a waist by an additional lens (not shown), and then can expand to fill the GRIN lens 410. The additional lens may be positioned between the mirror 420 and the GRIN lens 410 according to some embodiments of the invention, and may be used to cause the GRIN lens to focus the beam past its final surface and onto a rough metallic surface positioned at the distal end of the probe.

For clarity, the arm 406 is shown in a stretched out top view, but in practice rotation can occur at any of the right angle, 45° mirror elbows 412-420. Thus, the point 422 may be positioned approximately on a circle of radius 424 centered at point 426, and the point 428 may be positioned approximately on the surface of a sphere of radius 430 centered at point 422. In principle point 428 may be positioned anywhere within a torus of major and minor radii 424 and 430, respectively. According to some embodiments of the invention, major radius 424>>minor radius 430 and the useful working volume is approximately a circular cylinder of diameter and height that is two times the minor radius 430, located the distance of the major radius 424 from the base and a further distance 432 from the spectrometer 400. The base may be located at or near the mirror 404. The last two elbows 418, 420 can point the GRIN lens 410 in any direction. According to some embodiments of the invention, the distance 432 is between about 5 cm and about 50 cm, the major radius 424 is between about 20 cm and about 100 cm, and the minor radius 430 is between about 10 cm and about 50 cm. More or fewer mirror elbows 412-420 can be included depending on the requirements of the system, for example, the position and orientation of the spectrometer 400 with respect to the region of interest.

Figure 5:
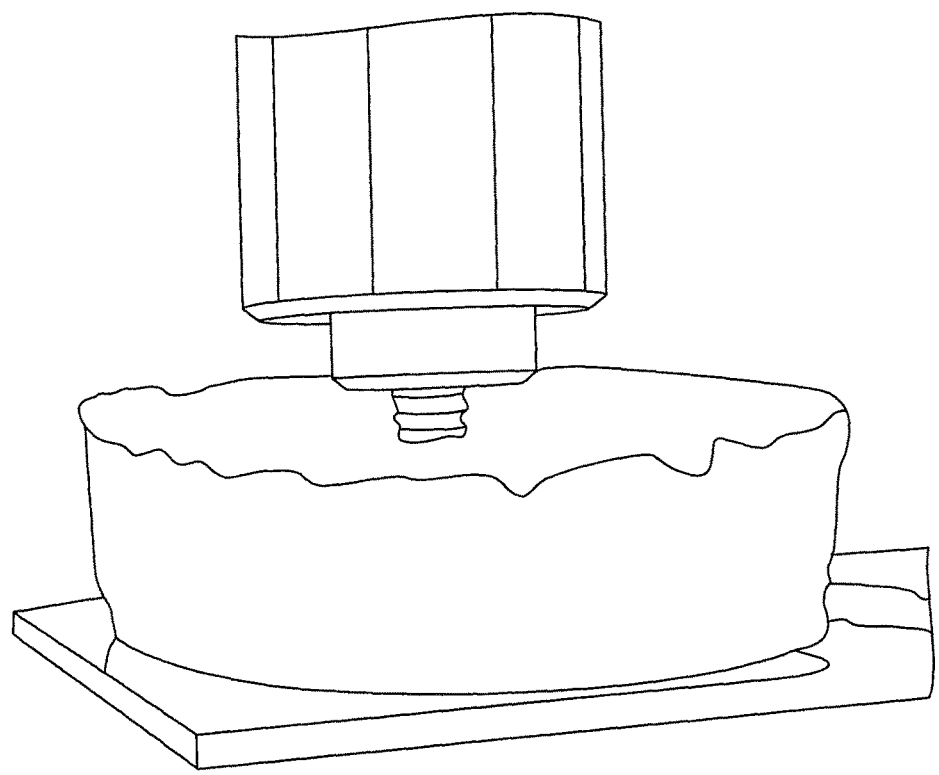
FIG. 5 shows a contact-type endoscope SERS probe inserted into a block of gelatin.
Figure 6:
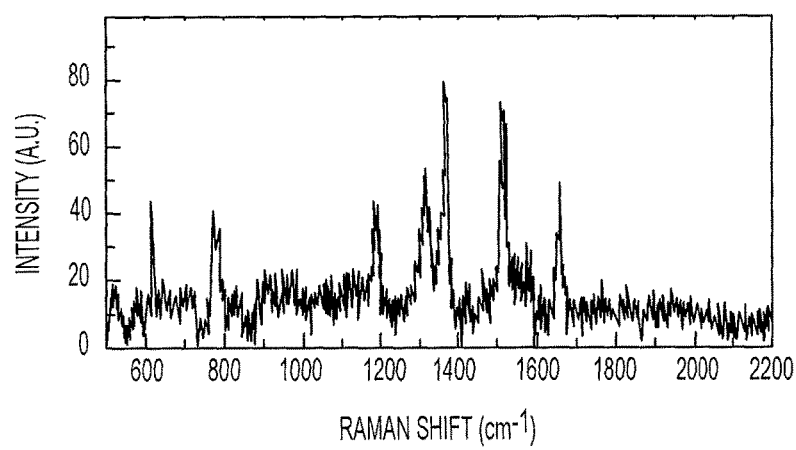
FIG. 6 shows the Raman spectrum obtained by pressing the probe against the surface of a gelatin sample.

The SERS probe of FIG. 4 was pressed against the surface of a gelatin sample, as shown in FIG. 5, and Raman spectra were obtained. The gelatin was prepared with a 1 mM solution of Rhodamine 6G substituted for water. FIG. 6 shows the Raman spectrum obtained by pressing the probe against the surface of the gelatin sample. The signal is characteristic of the Rhodamine 6G dye. To our knowledge this is the first time a SER spectrum has been obtained with access to only one side of a solid specimen. In addition, the narrow probe diameter facilitates obtaining spectra within a specimen.

As shown in FIG. 3, the SERS probe 300 according to some embodiments of the invention includes a GRIN lens 302 with a rough metallic layer 306 permanently attached to a transparent substrate 304 adhered to the distal end of the GRIN lens 302. The following describes methods and materials for forming the rough metallic surface 306. The inherent nanostructures present in aluminum and sputtered gold are used to enhance the Raman signals. Both in vitro structures for conventional examination of transparent specimen and in vivo probes for clinical applications[6] are described. The small diameter of the remotely positioned probe allows it to be minimally invasive in a clinical environment, so that SERS may be performed on a patient simply sitting or lying near the spectrometer.

Figures 7, 8:
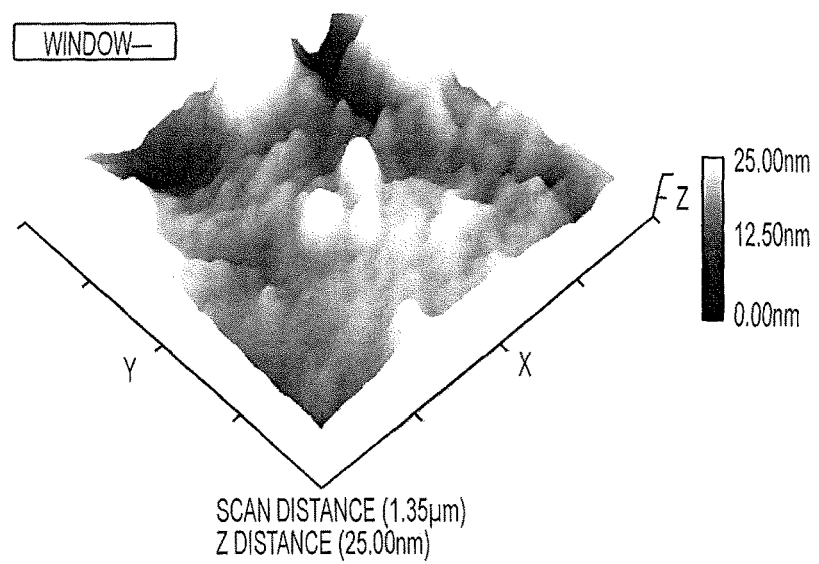
FIG. 7 shows relative signal strengths of substrates used for Raman spectroscopy.
FIG. 8 shows an atomic force microscope (AFM) image of a 20 nm layer of gold sputtered on stirred and etched aluminum.

The ability of various aluminum surfaces to enhance the Raman signal was studied using a LabRAM spectrometer (HORIBA Scientific, 3880 Park Avenue, Edison, N.J. 08820) operating at 633 nm. In each case the light was focused on the aluminum surface through a 1 mM solution of Rhodamine 6G. The table in FIG. 7 shows relative signal strengths of substrates used for Raman spectroscopy. The pellet and the sample of stock aluminum had only one useful face, characterized by a relatively smooth surface. The results for the transparent epoxy-gold combination are shown for transmission of the light through the substrate. Similar values of enhancement were found for both front and back sides of ordinary household aluminum foil, an aluminum pellet of 99.999% pure aluminum, and a sample of shop grade aluminum. The enhancement values are shown in the upper three rows of the table in FIG. 7. The performance of the aluminum foil is interesting in view of its low cost, about 0.005 cents for a 1 $cm^2$ sample.

Figure 9:
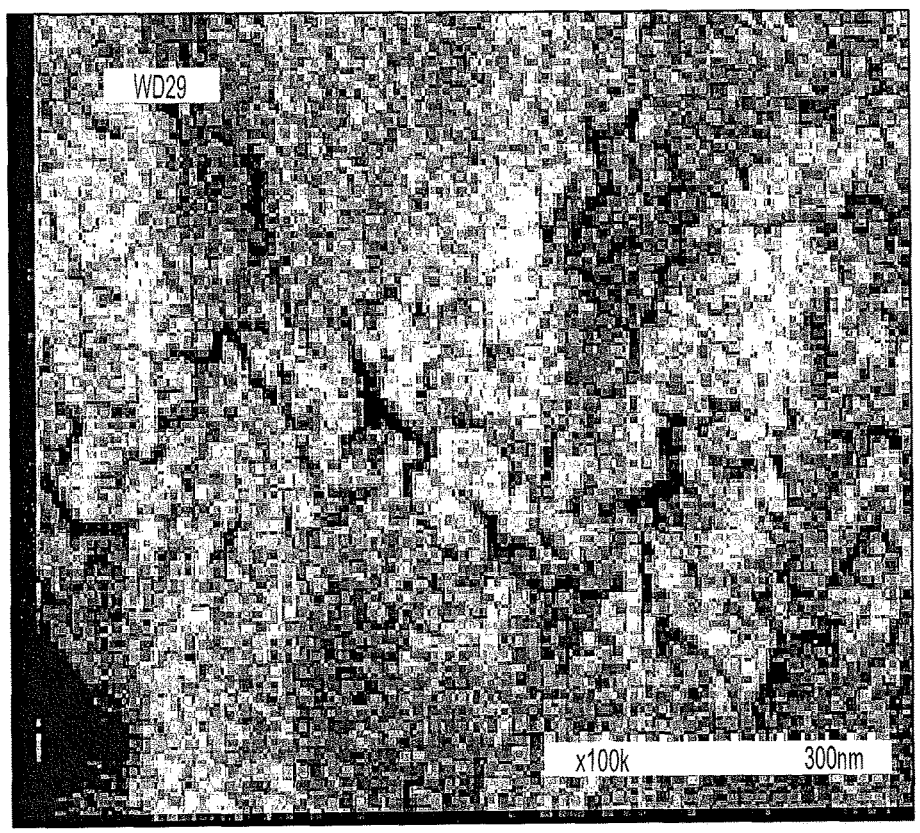
FIG. 9 shows a scanning electron microscope (SEM) image of a 20 nm layer of gold sputtered on stirred and etched aluminum.

The addition of 20 nm of sputtered gold dramatically increases the Raman enhancement. It has also been observed that observed that the location of the sample in the chamber in which the gold is sputtered has a strong effect on the Raman enhancement. The gold is sputtered onto aluminum foil, aluminum pellets, and transparent epoxy. The values for the gold-sputtered aluminum are shown in the fourth and fifth rows of the table in FIG. 7. The results for the transparent epoxy-gold combination, shown in the bottom row of the table, are for transmission of the light through the substrate. The increase in the Raman enhancement is much greater when the aluminum is first etched in a 30% KOH solution at room temperature for 1 minute. The increase is much stronger on the back or duller side of the aluminum foil, especially when the solution is stirred during etching. Since a smooth layer of gold would have little or no enhancement, it is speculated that the enhancement arises from the morphology of the combined gold and aluminum structure. The structure is shown in FIGS. 8 and 9, which show an atomic force microscope (AFM) image and a scanning electron microscope (SEM) image, respectively, of a 20 nm layer of gold sputtered on stirred and etched aluminum.

Figure 10A:
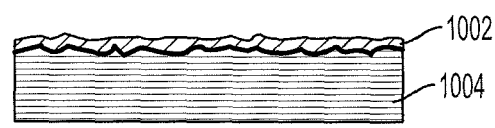
FIG. 10A illustrates the deposition of a metallic layer on aluminum foil according to some embodiments of the invention.
Figure 10B:
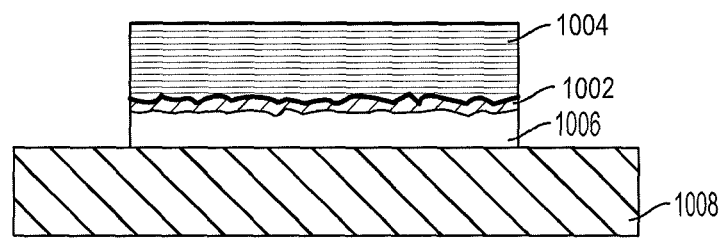
FIG. 10B illustrates how aluminum foil with the metallic layer is bonded with UV curing epoxy or other adhesive to a glass microscope slide or cover slip, or directly to the GRIN lens.
Figure 10C:
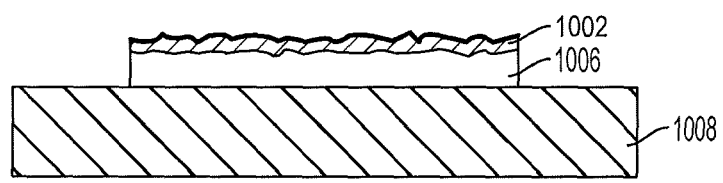
FIG. 10C illustrates how the aluminum foil is removed by etching.
Figure 11:
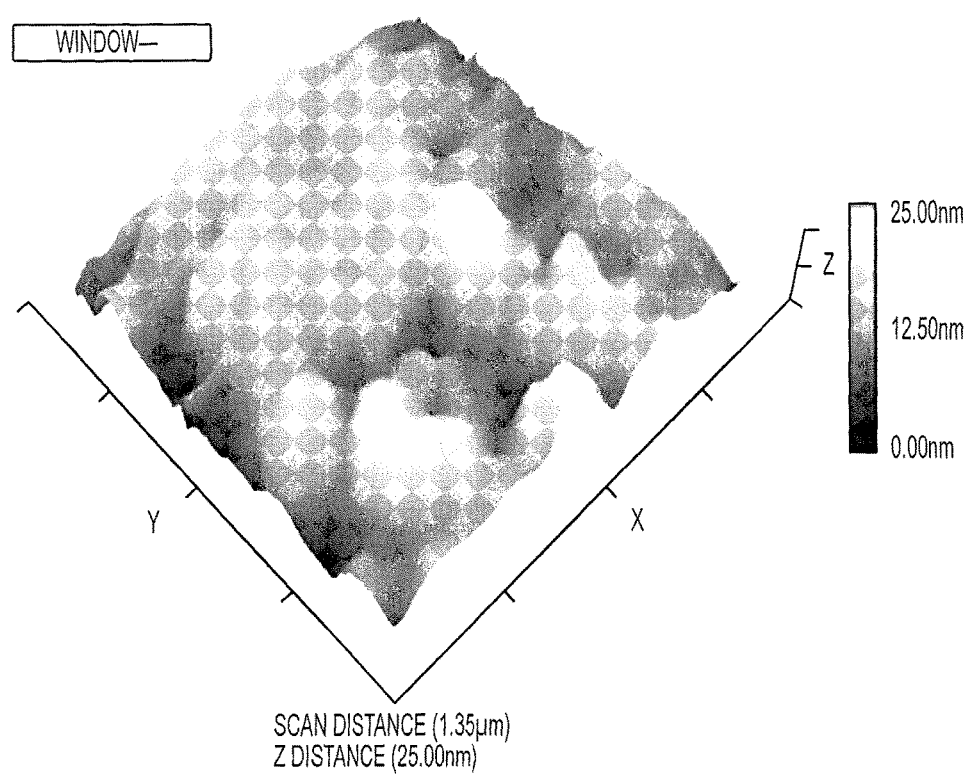
FIG. 11 shows an AFM image of a 20 nm layer of gold on epoxy.

For in vivo applications, the signal enhancing layer can be bonded by a transparent substrate to a GRIN lens. FIGS. 10A-10C illustrate the process for bonding the signal enhancing layer to the GRIN lens according to some embodiments of the invention. The fabrication of a signal enhancing layer on a transparent substrate starts with the deposition of a metallic layer 1002 on aluminum foil 1004, illustrated in FIG. 10A. According to some embodiments of the invention, the metallic layer 1002 can be a layer of gold. The metallic layer 1002 can have a thickness between about 10 nm and about 30 nm according to some embodiments of the invention, and a thickness between about 15 nm and about 25 nm according to some embodiments of the invention. The aluminum foil 1004 may first be etched, for example in a 30% KOH solution at room temperature for 1 minute. Other concentrations and etching times may be employed, with the etching time generally increasing as the concentration decreases. Other etching solutions may be used, for example, NaOH. The aluminum foil 1004 with the metallic layer 1002 is subsequently bonded with UV curing epoxy 1006 or other adhesive to a glass microscope slide or cover slip, or directly to the GRIN lens 1008. This is illustrated in FIG. 10B. The aluminum foil 1004 is then removed by etching, as shown in FIG. 10C. For example, the aluminum foil 1004 may be etched in a 6% KOH solution at room temperature for 2 hours. Other concentrations and etching times may be employed, with the etching time generally increasing as the concentration decreases. Other etching solutions may be used, for example, NaOH and other acids or bases. FIG. 11 shows an AFM image of a 20 nm layer of gold on epoxy, highlighting the roughness of the layer of gold The UV curing epoxy (Norland Optical Adhesive 68, Edmund Optics America) is a clear optical cement and introduces very little Raman background. The embodiments of the invention are not limited to this epoxy, and other transparent substances may be used to adhere the gold layer to the GRIN lens. The gold is also thin enough to be partially transparent. The epoxy plays an important role in adhering the gold to the GRIN lens, since the head of the probe must be ruggedly constructed. The ruggedness allows the probe to be pressed against, or into, a specimen. The gold by itself does not adhere well to most material, and therefore the epoxy is employed to act as a strong glue that adheres the gold to the GRIN lens.

Figure 12:
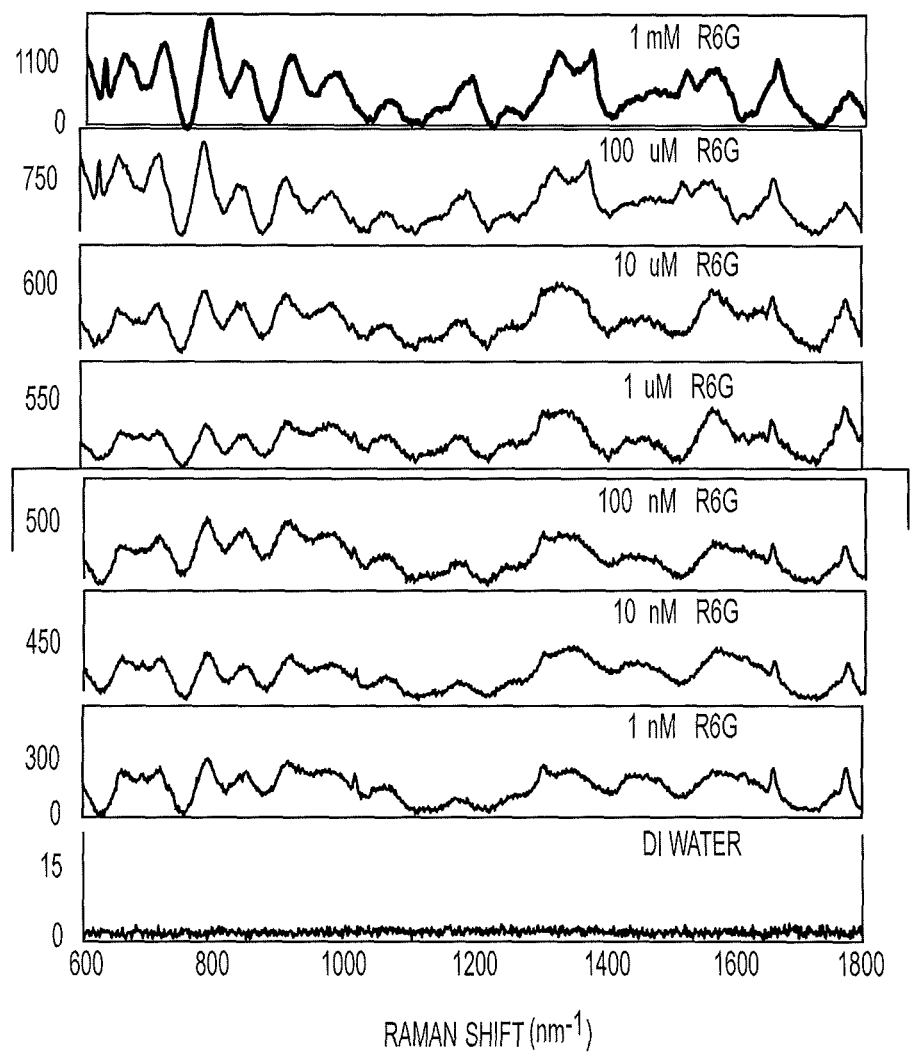
FIG. 12 shows the strength of the Raman signal for individual scans with various concentrations of Rhodamine 6G dye in distilled water.
Figure 13:
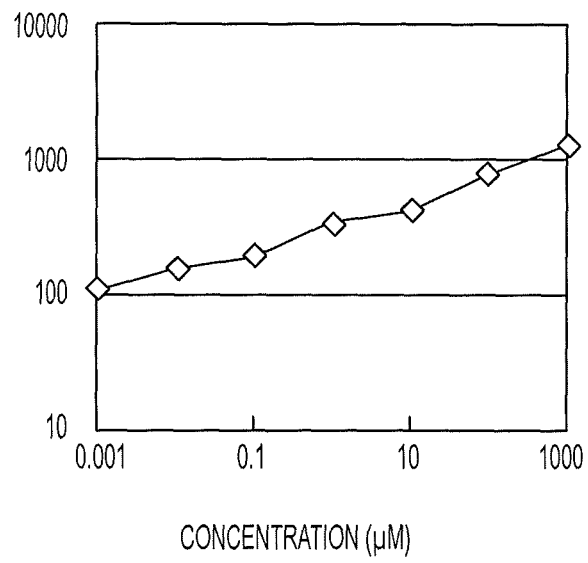
FIG. 13 shows the peak height of the Raman signal versus the concentration of Rhodamine 6G dye in distilled water.

The performance of the gold on an epoxy substrate was evaluated by measuring the strength of the Raman signal for various concentrations of Rhodamine 6G dye in distilled water. FIG. 12 shows the signal strength for individual scans, and FIG. 13 shows the peak height versus the concentration for an average of multiple scans at each concentration. The signal strength varies by slightly more than a factor of 10 when the concentration of the dye is varied by a factor of $10^6$. The data displayed in FIGS. 12 and 13 highlights the effect of the surface enhancement of the Raman spectrum. Although the concentration is decreased by a very large factor, the enhanced signal decreases much more slowly.

Methods have been demonstrated for fabricating nano-rough metallic surfaces to enhance Raman signals. Bare aluminum provides some enhancement, with the least costly source being household aluminum foil. No significant differences were found between the two sides of the foil. For the purest aluminum the signal strength is improved by etching. The addition of a 20 nm layer of sputtered gold dramatically increases the signal strength. The effect is particularly strong when the aluminum has previously been etched, especially when the etching solution is stirred during etching. As mentioned above, it was also observed that the location of the sample in the chamber in which the gold was sputtered has a strong effect on the Raman enhancement. The sputtered gold film can be bonded to a glass substrate or GRIN lens with a clear UV curing epoxy, and the aluminum subsequently removed by etching. This can be incorporated into a probe coupled to a remote spectrometer, so that SERS may be performed on a patient simply sitting or lying near the spectrometer.

According to some embodiments of the invention, aluminum foil is smoothed by a preliminary etch in dilute KOH. A thin layer of gold, between about 10 nm and about 30 nm, is deposited on the aluminum, followed by spin casting between about 0.5 microns and about 1.5 microns of PMMA. The PMMA forms a hard, brittle layer. It is covered with between about 0.5 mm and 1.5 mm thick clear resin, much softer than the PMMA, especially during its curing time of several hours. The other side of the resin is supported, for example by a glass microscope slide. While the resin is still relatively soft a small diameter rod is forcefully rolled across the aluminum foil, fracturing the PMMA layer into small tiles, which remain adhered both to the gold coated aluminum and to the resin. A second KOH etch removes the aluminum, exposing the gold covered PMMA tiles. This has already demonstrated enhancements compa-rable to the best methods previously used, and it is possible that optimization of the parameters will lead to still greater enhancements.

Additional methods for preparing the metallic surface are now described. In one approach, a layer of gold with a thickness between about 10 nm and about 30 nm is sputtered on the polished surface of a silicon wafer. Gold is chosen over silver, which also has SERS properties, for its long term stability and poor adherence to silicon. A drop of UV curing epoxy[7] was placed on the wafer and mechanically spread to a thickness between about 0.5 mm and about 1.5 mm by pressing with a flexible plastic foil. The epoxy chosen is ordinarily used as a "lens bond" to cement optical components, and is transparent at visible wavelengths. According to some embodiments, the epoxy is hardened after about 5 minutes under a 13 W UV lamp. Higher power lamps, longer exposure times, and more sensitive UV epoxies are all well known and can be employed. In some lithographic applications, liquid epoxy cast on a silicon wafer and shaped by a template is hardened in about 1 second. Once the epoxy is hardened, the foil and the epoxy are readily peeled off the silicon wafer. Gold's poor adherence facilitates the peeling by acting as a mold release. Some gold remains on the epoxy as a non-continuous layer. The transmission of the gold covered epoxy is about 35%. This process produces useful enhanced Raman signals. However, sputtering additional gold directly on the epoxy further enhances the Raman scattering signal.

The Raman scattering signal can be enhanced even more by etching the silicon wafer to roughen its surface before the gold is deposited. The etching can be a dry, reactive ion etch, or the combination of a wet etch followed by the dry etch. The reactive ion etch uses SF6 to remove about 200 nm of silicon. The wet etch is in an electric field on highly doped (0.001 Ω·cm) p-type (100) silicon wafers. They are etched for 3 minutes in a 3:7 solution of 48% HF in ethanol in a cell between about 15 mm and about 25 mm in diameter and between about 40 mm and 55 mm long.[8] Other concentrations and times may be used for etching, with higher concentrations and longer etch times producing larger holes in the silicon wafers.

Figure 14:
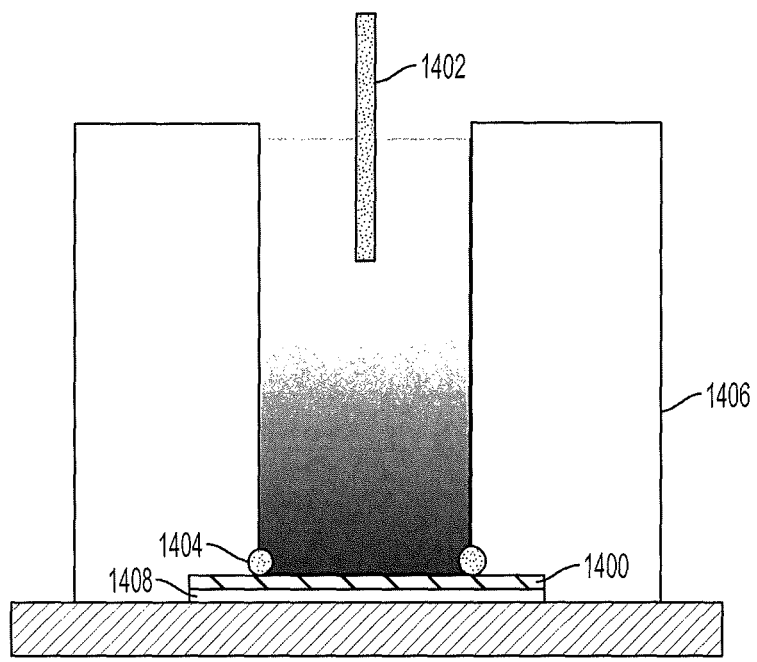
FIG. 14 shows an apparatus for etching silicon according to some embodiments of the invention.

FIG. 14 shows an apparatus for etching the silicon 1400. A voltage is applied to the cell via a platinum wire 1402 which acts as a cathode. The voltage can between about 1.5 V and about 5V. The etched area is defined by an O-ring 1404 and a Teflon block 1406. The silicon 1400 may be situated on top of a layer of aluminum foil 1408, which acts as an anode. The applied voltage can result in a current density between about 11.7 and about 14.3 mA/cm². The O-ring 1404 has a diameter between about 10 mm and about 50 mm according to some embodiments of the invention. The etching starts as closely spaced narrow holes which are undercut as the holes deepen. The subsequent reactive ion etch exposes the wider subsurface openings, further roughening the silicon surface. According to some embodiments, the reactive ion etch is in $SF_6$ at between about 190 W and about 210 W for between about 8 s and about 12 s.

Figure 15A:
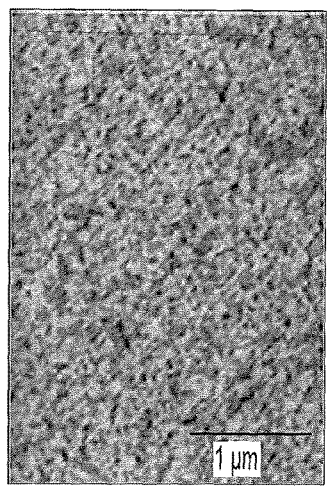
FIG. 15A shows a 1 KV scanning electron microscope (SEM) image of the surface of a wafer after a wet etch.
Figure 15B:
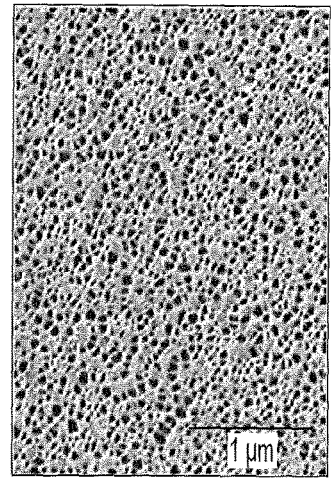
FIG. 15B shows a 1 KV SEM image of a similar area as in FIG. 15A after the subsequent reactive ion etch.
Figure 15C:
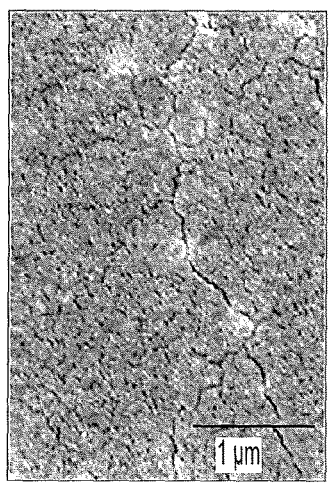
FIG. 15C shows a 1 KV SEM image of the epoxy substrate cast on a dry etched wafer and covered with 60 nm of gold.
Figure 15D:
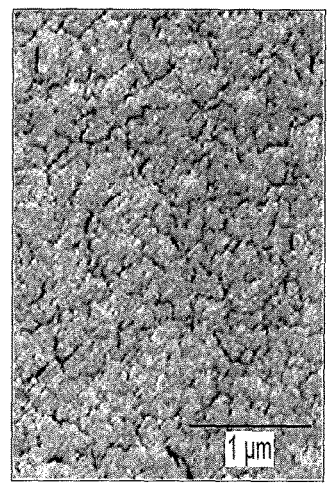
FIG. 15D shows a 1 KV SEM image of the epoxy substrate cast on a both wet and dry etched wafer and covered with 60 nm of gold.
Figure 15E:
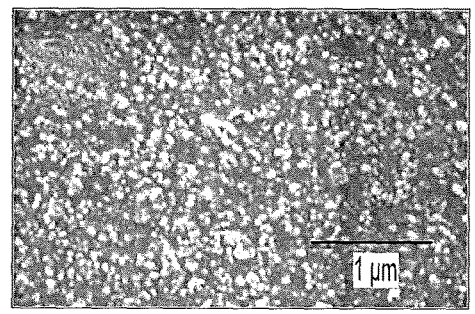
FIG. 15E shows an SEM image at 3 KV of an epoxy substrate cast on a both wet and dry etched wafer and covered with 40 nm of gold.

FIG. 15A shows a 1 KV scanning electron microscope (SEM) image of the surface of a wafer after the wet etch, and FIG. 15B shows a similar area after the subsequent reactive ion etch. 1 KV SEM images were also taken of the epoxy substrate after additional gold deposition. FIG. 15C shows the epoxy substrate cast on a dry etched wafer and covered with 60 nm of gold. FIG. 15D shows the epoxy substrate cast on both wet and dry etched wafer and covered with 60 nm of gold. Because the epoxy was cast on the silicon the images might be expected to be complimentary. However, they are very different. This difference arises in part because the electron range in gold is only about $\frac{1}{8}^{th}$ its range in silicon. The electron range at 3 KV in gold is comparable to the range at 1 KV in silicon and an image of the gold surface at 3 KV, taken with a different SEM and shown in FIG. 15E, more nearly corresponds to the 1 KV silicon image. Although the 1 KV images indicate the presence of very small features in the gold, uncertainties in the image formation of the two SEMs preclude a direct depiction of the gold surfaces. However, this was also obtained with an AFM. FIG. 16A shows an AFM image of 40 nm of gold on epoxy substrates cast on a dry etched wafer and FIG. 16B shows an AFM image of 40 nm of gold on epoxy substrates cast on a both wet and dry etched wafer. The height distributions across the marked 1 micron lines are shown below the AFM images. The wet and dry etched sample is much rougher, with an RMS height variation of 32 nm as compared to an RMS height variation of 14 nm for the wet etched wafer. The corresponding peak to valley variation is 600 nm to 250 nm. The greater roughness of the wet and dry etched wafer increases the plasmon enhancement.

Test cells were constructed in which the clear epoxy substrates were sandwiched between a microscope slide and a cover slip. This setup is illustrated in FIG. 17. The microscope objective is shown focusing light from the Raman spectrometer onto the gold surface of the epoxy substrate. Turning the cell upside down focuses the light through the cover slip and the epoxy substrate. The active volumes of the cells were about 0.1 mL. They were filled and emptied via 1 mm ID stainless steel and rubber tubes. Rhodamine 6G was used a test material, and solutions of it dissolved in DI water were pumped through the cells from a syringe.

Raman spectra were obtained with a Raman spectrometer[9] operating with a 1 mW 633 nm laser beam and a 5 second integration time. A 50×NA=0.55 long working distance microscope objective[10] was used to focus the laser beam either on the front surface of the gold through the microscope slide and the Rhodamine 6G solution, or on the back surface of the gold through the cover slip and the clear epoxy substrate (see FIG. 17). Stock solutions of Rhodamine 6G were prepared, ranging by factors of 10 in concentrations from 1 nM to 1 mM. The solutions were introduced into test cells, such as the cell shown in FIG. 17. A microscope objective 1700 focused light through a microscope slide 1702 and a flow of Rhodamine 6G solution 1704 and onto a layer of gold 1706. The layer of gold 1706 was adhered to an epoxy substrate 1708, which was in turn adhered to a cover slip 1710. Alternatively, the test cell could be turned upside down to focus the light onto the layer of gold 1706 through the cover slip 1710 and the epoxy substrate 1708. To minimize possible contamination of the cells the solutions were studied in order, from the lowest concentration to the highest. At least 1 mL of each solution was pumped through the cells to flush out any remaining solution of the lower concentration.

Figure 18:
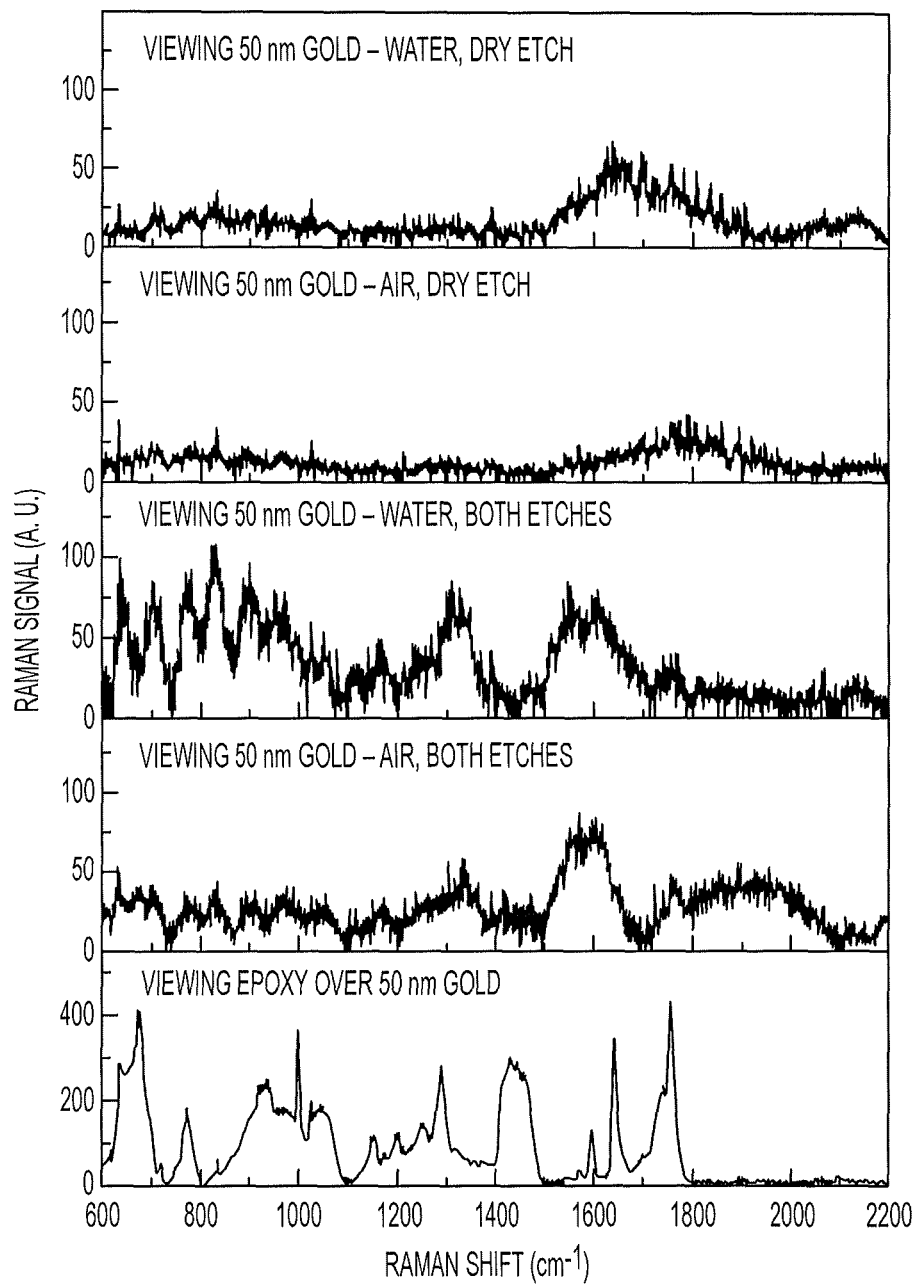
FIG. 18 shows background signals for the empty and water filled cells.

Contributions to the Raman scattering signal arising from the materials used to construct the cells were evaluated by obtaining Raman spectra with the cells both empty and filled with DI water. FIG. 18 shows background signals for the empty and water filled cells. The spectrometer was focused on the front surface of the gold. The strongest signal is from light focused on the epoxy substrate. The signal from the epoxy was obtained with the spectrometer focused on the back surface of the gold, through the epoxy. None of the background signals show a peak at 1362 cm$^{-1}$, the reference peak that was used as a measure of the Rhodamine 6G signal.[11,12]

Figure 19:
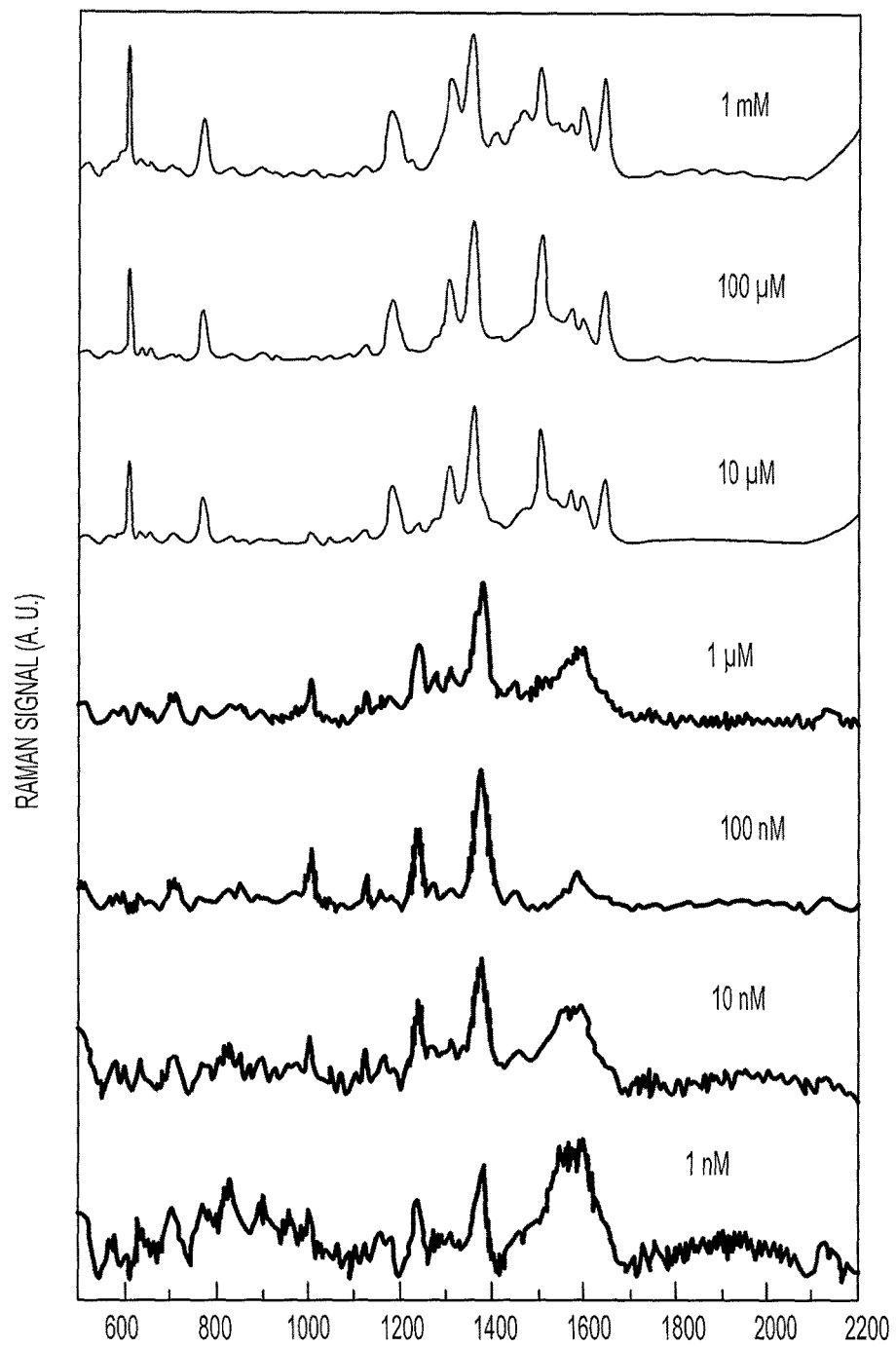
FIG. 19 shows Raman spectra obtained with 80 nm of gold in contact with the Rhodamine 6G solutions.

FIG. 19 shows Raman spectra obtained with 80 nm of gold in contact with the Rhodamine 6G solutions. The gold was deposited on an epoxy substrate that was cast on a silicon wafer that had been both wet and dry etched. The Rhodamine 6G concentrations vary by factors of 10 from 1 mM to 1 nM. The strongest Raman scattering signals were obtained with light focused through the solutions to the surface of the epoxy substrate on which an additional 80 nm of gold had been sputtered.

Figure 20:
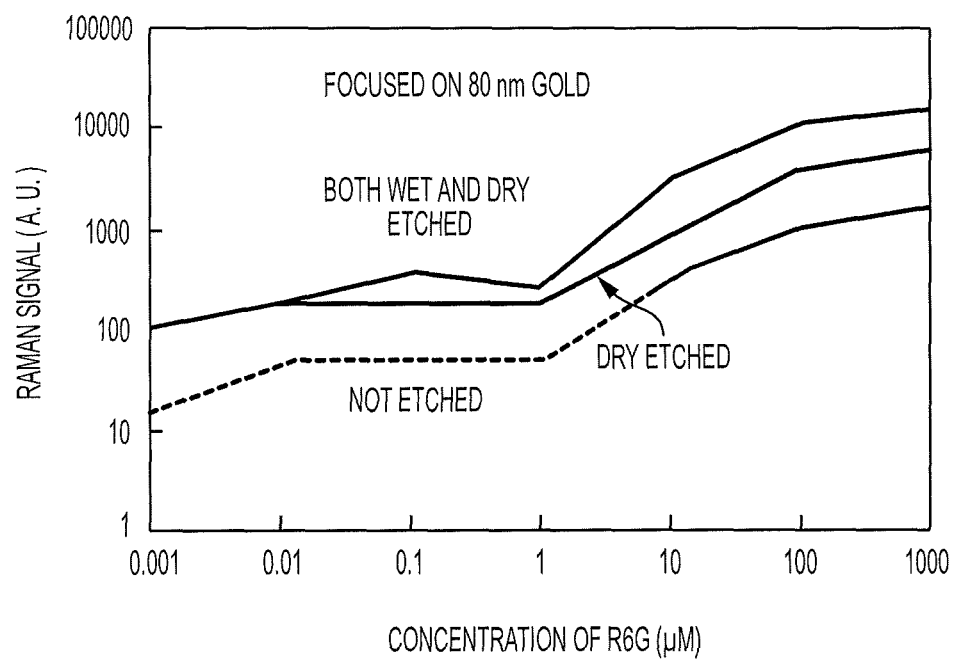
FIG. 20 shows the Raman signal as a function of concentration of Rhodamine 6G for an unetched wafer, a dry etched wafer, and a wafer that is both wet and dry etched.
Figure 21:
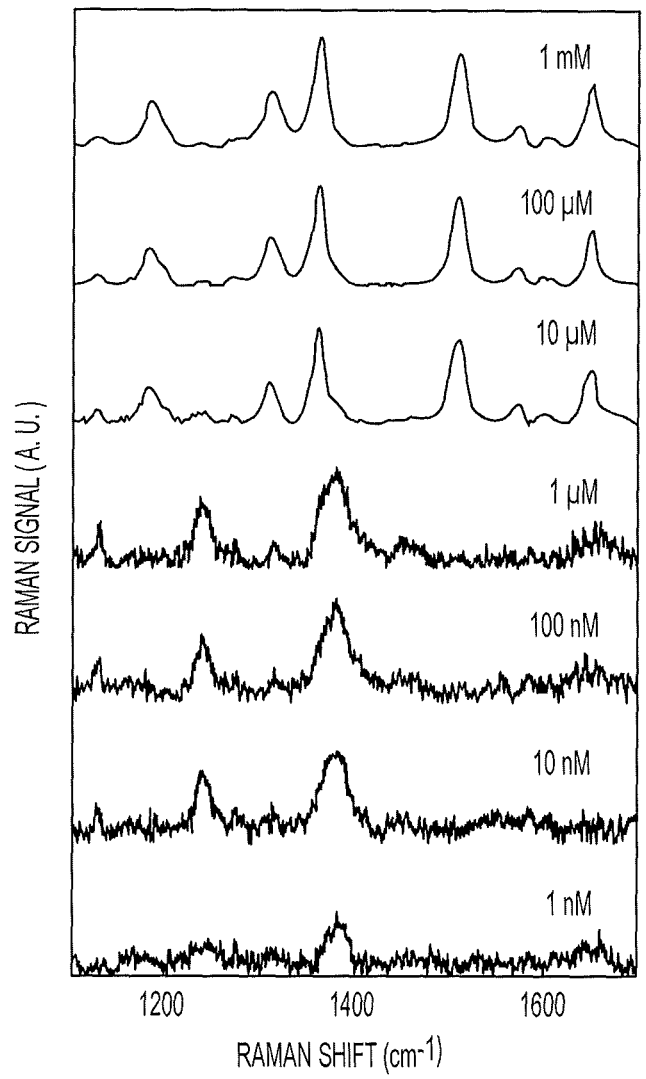
FIG. 21 shows surface enhanced Raman spectra obtained with no preliminary etching of the silicon wafer from which the epoxy substrate was cast.

FIG. 20 illustrates the effects of etching the silicon wafer from which the epoxy substrate was cast. The plots in FIG. 20 show signals obtained over the full range from 1 nM to 1 mM for all three methods of preparation of the epoxy substrate. Stronger surface enhanced Raman signals, measured at the 1362 cm$^{-1}$ line, were obtained after etching. The dotted curve reflects a change in spectrum at lower concentrations for the not etched case, with additional details provided in FIG. 21. However, the signals were strongest for the epoxy cast on double etched silicon wafers. FIG. 21 shows surface enhanced Raman spectra obtained with no preliminary etching of the silicon wafer from which the epoxy substrate was cast. Below 1 μM the spectrum from epoxy cast on smooth, unetched wafers changed[13-15] but the reference peak at 1362 cm$^{-1}$ remained.

Figure 22:
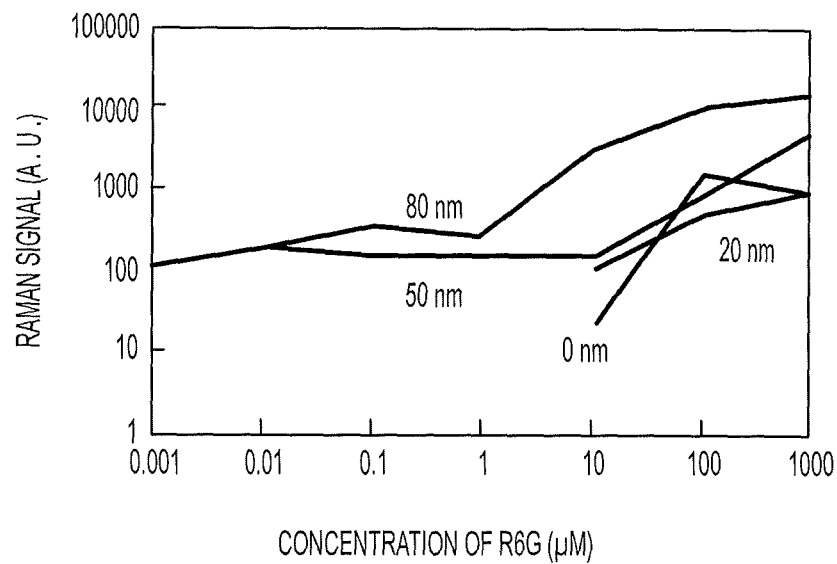
FIG. 22 shows the effect of various thicknesses of additional gold on the surface enhanced Raman signal.

Surface enhanced Raman scattering was observed for light focused through the solutions to the gold surface even with no additional gold added to the epoxy substrate. These signals evidently arose because some of the gold used for mold release adhered to the epoxy. Sputtering additional gold significantly increased the observed signal strengths, as shown in FIG. 22. Signals from Rhodamine 6G concentrations less than 10 μM required at least 50 nm of gold to be observable.

Figure 23:
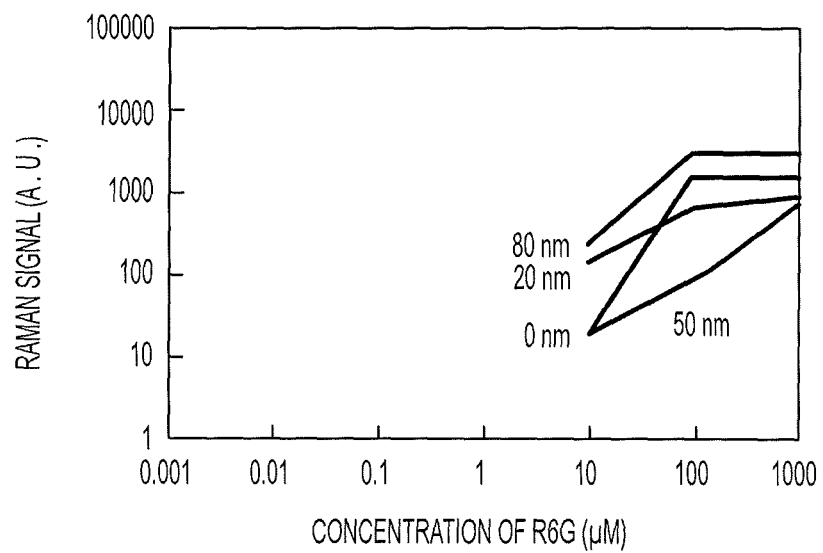
FIG. 23 shows surface enhanced Raman signals from Rhodamine 6G solutions viewed through a transparent substrate.

Light entering through the epoxy side of the sample must make two passes through the gold. The measured transmission was about 30% per 20 nm of gold. It was slightly higher for 20 nm or less of additional gold deposited on epoxy cast over roughened silicon, although that interface appeared dark when viewed through the epoxy. FIG. 23 shows surface enhanced Raman signals from Rhodamine 6G solutions viewed through the transparent substrate. Useful signals were only obtained in the range of concentrations from 10 μM to 1 mM.

Surface enhanced Raman scattering utilizes a metallic surface that is rough at the nanoscale. This work demonstrates how such surfaces may be obtained on a transparent substrate with minimal effort. The transparent substrate according to some embodiments of the invention was a UV curing epoxy cast on a silicon wafer. A layer of gold sputtered on the wafer acted as a mold release because the adherence between the epoxy and the gold was better than that between the gold and the silicon. The gold was sufficiently rough to enhance Raman scattering from a solution of Rhodamine 6G dye. Pre-etching the silicon wafer with wet and/or dry etches increased the roughness of the wafer and the epoxy, and therefore the strength of the Raman signal. Additional gold deposited directly on the epoxy also increased the Raman signal. Signal to noise ratios of greater than 10:1 were obtained with solutions of Rhodamine 6G down to 1 nM.

Simple cells were described in which light from a Raman spectrometer was focused both through the Rhodamine 6G solutions and through the epoxy substrate. The advantage of a clear substrate is that it can be placed at the end of a probe instead of in a cell. For example, the clear substrate may be adhered to a GRIN lens that is part of a contact-type endoscope SERS probe. However, since the light must pass through the gold in this configuration the thickness of any additional gold should be carefully considered. The probe can then be placed against, or inside, the specimen whose Raman spectrum is to be studied.

REFERENCES

[1] Fleischmann M., Hendra P. J., and McQuillan A., Chem. Phys. Lett. 26, 163 (1974).
[2] Van Duyne R. P., J. Phys. (Paris) 38, C5-239 (1977).
[3] Liu G. L. and Lee L. P., Appl. Phys. Lett. 87, 074101 (2005).
[4] Gersten J. I., J. Chem. Phys. 72, 5779 (1980).10.1063/1.439002
[5] Nie S. M. and Emory S. R., Science 275, 1102 (1997).
[6] J. Kim et. al./Vac. Sci. Technol., vol. B-31, no. 6, November/December, 2013.
[7] Norland Optical Adhesive 68, Edmund Optics America, Barrington, N.J.
[8] Malempati P. R., Master's thesis, Louisiana State University (2011).
[9] LabRAM Raman spectrometer, HORIBA Scientific, Edison, N.J.
[10] Olympus ultra-long working distance MS plan 50× objective, Olympus Corporation, Center Valley, Pa.
[11] Weiss A. and Haran G., J. Phys. Chem. B 105, 12348 (2001).
[12] Hildebrandt P. and Stockburger M., J. Phys. Chem. 88, 5935 (1984).
[13] Kudelski A., Chem. Phys. Lett. 414, 271 (2005).
[14] Kudelski A. and Pettinger B., Chem. Phys. Lett. 383, 76 (2004).
[15] Wang Z. and Rothberg L. J., J. Phys. Chem. B 109, 3387 (2005).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for contact-type endoscope surface enhanced Raman scattering (SERS) comprising:
   a Raman spectrometer;
   a probe having a proximal end and a distal end, comprising:
   a gradient-index (GRIN) lens; and
   a rough metallic layer optically connected to said GRIN lens; and
   an articulated arm comprising a plurality of mirrors for reflecting an illumination light from said Raman spectrometer to said probe, and for reflecting a scattered light from said probe to said Raman spectrometer,
   wherein said rough metallic layer is configured to contact a sample such that the rough metallic layer is positioned between the GRIN lens and the sample; and
   wherein said GRIN lens focuses said illumination light from said Raman spectrometer onto said rough metallic layer.

2. A system for contact-type endoscope SERS according to claim 1, wherein said rough metallic layer is positioned at said distal end of said probe.

3. A system for contact-type endoscope SERS according to claim 1, wherein said Raman spectrometer further comprises a light source for providing said illumination light, wherein said light source is a HeNe laser source.

4. A system for contact-type endoscope SERS according to claim 1,
   further comprising a transparent substrate adhered to said GRIN lens between said GRIN lens and said rough metallic layer.

5. A system for contact-type endoscope SERS according to claim 1,
   further comprising a transparent substrate adhered to said rough metallic layer between said GRIN lens and said rough metallic layer.

* * * * *